(12) United States Patent
Frese et al.

(10) Patent No.: US 10,426,384 B2
(45) Date of Patent: Oct. 1, 2019

(54) GLUCOSE SENSOR

(71) Applicant: FRAUNHOFER-GESELLSCHAFT ZUR FÖRDERUNG DER ANGEWANDTEN FORSCHUNG E.V., München (DE)

(72) Inventors: Ines Frese, Mainz (DE); Thomas Klotzbücher, Mommenheim (DE)

(73) Assignee: FRAUNHOFER-GESELLSCHAFT ZUR FÖRDERUNG DER ANGEW ANDTEN FORSCHUNG E.V, Munich (DE)

( * ) Notice: Subject to any disclaimer, the term of this patent is extended or adjusted under 35 U.S.C. 154(b) by 319 days.

(21) Appl. No.: 15/312,247

(22) PCT Filed: Jun. 2, 2015

(86) PCT No.: PCT/EP2015/062206
§ 371 (c)(1),
(2) Date: Nov. 18, 2016

(87) PCT Pub. No.: WO2015/185529
PCT Pub. Date: Dec. 10, 2015

(65) Prior Publication Data
US 2017/0086716 A1    Mar. 30, 2017

(30) Foreign Application Priority Data
Jun. 3, 2014   (DE) .................. 10 2014 210 440

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/1459* (2013.01); *A61B 5/1495* (2013.01);
(Continued)

(58) Field of Classification Search
CPC ............ A61B 5/14532; A61B 5/14528; A61B 5/6852; A61B 5/1495; A61B 5/1459;
(Continued)

(56) References Cited

U.S. PATENT DOCUMENTS

2004/0072358 A1 * 4/2004 Ballerstadt ......... A61B 5/14532
436/95
2005/0113658 A1    5/2005 Jacobson et al.
(Continued)

FOREIGN PATENT DOCUMENTS

DE          103 11 452 A1    10/2004
DE    10 2004 055 032 A1     8/2006
(Continued)

OTHER PUBLICATIONS

Mohammadi, L.B., et al., A minimaly invasive chip based near infrared sensor for continuous glucose monitoring, Proc. of SPIE, vol. 8427, pp. 84270K-1-84270K-11, 2012.

*Primary Examiner* — Eric F Winakur
*Assistant Examiner* — Abid A Mustansir
(74) *Attorney, Agent, or Firm* — Hudak, Shunk & Farine Co. LPA

(57) ABSTRACT

A method for determining the glucose value in blood or in interstitial liquids and to a glucose sensor including a catheter which has one or more openings in the region of the distal end of the catheter; a first optical waveguide which is arranged in the catheter and which includes a coupling surface at the distal end of the optical waveguide; a measuring probe which is arranged in the region of the distal end of the catheter, is coupled to the coupling surface of the first optical waveguide, and has a mirror arranged opposite the coupling surface of the first optical waveguide and a detection chamber between the coupling surface of the first optical waveguide and the mirror; a detection liquid for glucose in the detection chamber; and a membrane which (Continued)

encloses at least the detection chamber filled with the detection liquid and which has a separation capacity of maximally 20 kDA.

18 Claims, 3 Drawing Sheets

(51) Int. Cl.
    *A61B 5/1459*      (2006.01)
    *A61B 5/1495*      (2006.01)
    *A61B 90/30*      (2016.01)

(52) U.S. Cl.
    CPC ........ *A61B 5/14528* (2013.01); *A61B 5/6848* (2013.01); *A61B 5/6852* (2013.01); *A61B 5/0022* (2013.01); *A61B 5/6876* (2013.01); *A61B 2090/306* (2016.02); *A61B 2090/309* (2016.02); *A61B 2560/0233* (2013.01); *A61B 2560/0443* (2013.01); *A61B 2562/168* (2013.01)

(58) Field of Classification Search
    CPC ............ A61B 5/6848; A61B 2090/306; A61B 2090/309; A61B 2560/0233; A61B 2560/0443; A61B 2562/168; A61B 5/0022; A61B 5/6876
    See application file for complete search history.

(56) References Cited

U.S. PATENT DOCUMENTS

2005/0154272 A1*    7/2005    Dirac ................ A61B 5/14532
                                                                        600/365
2009/0088615 A1     4/2009    Robinson et al.

FOREIGN PATENT DOCUMENTS

| | | |
|---|---|---|
| DE | 10 2009 010 955 A1 | 9/2010 |
| DE | 20 2007 019 544 U1 | 8/2013 |
| WO | 99 07277 A1 | 2/1999 |

* cited by examiner

GLUCOSE SENSOR

FIELD OF THE INVENTION

The invention concerns a glucose sensor and a method for determination of the glucose value in blood or in interstitial fluid, especially in vivo determination in humans or animals.

BACKGROUND OF THE INVENTION

In practice, the measurement of the glucose concentration is usually done indirectly through an enzymatic conversion of the glucose with subsequent detection of the hydrogen peroxide released during the conversion reaction, being proportional to the glucose concentration, or the oxygen consumed, for example, by a color change reaction, a fluorescence measurement, or an electrochemical determination. For this, a blood sample is first placed on a test strip, for example. The drawback to this measurement based on enzymatic conversion of glucose is that it can only be performed discontinuously and therefore needs to be repeated often, and the test strip can only be used once. There is also a quasi-continuous measurement by means of an implanted, enzymatically functionalized sensor surface, based on enzymatic conversion of glucose. But the lifetime of such a sensor is limited by the progressive consumption of the enzyme. Furthermore, the consumption of the enzyme requires a readjusting or calibrating of the sensor at regular intervals (several times a day). Finally, the precision of the best sensors of this type in the relevant measurement range is around 50 to 250 mg/dl with a mean absolute error (MARE) of less than 10%.

DE 10 2009 010 955 A1 specifies a method and a measurement device for the determination of blood sugar values in the form of the glucose or fructose determination in human blood by means of optical spectroscopy. It is proposed to implant an optical, monolithic, miniaturized spectrometer in the human body, having a measurement cell in the form of a measurement fiber, which is introduced by its fiber end directly into the blood stream of a person. The measurement fiber has a recess at its distal end, constantly washed by blood, and a coupling site at its opposite proximal end, which is connected to a light-conducting disk. The light-conducting disk forms a unit with a silicon disk, on which is arranged an evaluating unit. The evaluating unit evaluates the measurement data, stores it or transmits it by telemetry to an insulin pump or a heart rate monitor for display. This arrangement records a remitted absorption spectrum of the scattered light in the blood stream of the person, from which the blood sugar value and/or other blood values are determined. The drawback to this method and measurement device is, in particular, that the recess in the measurement fiber forms a predetermined breaking point and increases the risk of the end of the measurement fiber breaking off during improper handling or careless movement of the patient, getting into the blood stream, and endangering the patient. Another drawback is that the absorption measurement in the blood can be influenced by other effects, such as a buildup of blood cells in the area of the recess, which would impair the glucose detection accuracy. Document US 2009/0088615 A1 teaches the same measurement principle.

Furthermore, there have been studies with the participation of the inventor on glucose determination by measurement of differential absorbance in the near infrared spectrum, as described for example in the article "A minimally invasive chip based near infrared sensor for continuous glucose monitoring", L. Ben Mohamadi et al, Proc. of SPIE Vol. 8427 84270K-1. In this method, a perfusion solution is pumped by means of a dialysis pump through a subcutaneously or intravenously applied dialysis needle (catheter), across a semipermeable membrane (typically with a separation capacity of 20 kDa), which is not permeable to blood cells and larger fat or protein molecules, but is so for the perfusate and the glucose, the glucose diffusing from the blood or interstitial fluid into the perfusate. The specimen (analyte) so obtained is transported into a microfluidic chip with infrared light source and a photosensitive detector (GaAs photodiode), where a change in the NIR absorption dependent on the glucose concentration is compared against a reference measurement at a reference cell filled with pure liquid. This so-called absorption difference measurement provides a measurement precision with a mean absolute relative error (MARE) of around 5%. The drawback to this measurement method, among other things, is the large distance between the sampling point of the analyte, i.e., the dialysis needle on the one hand, and the detection cell on the other hand, in conjunction with a low flow rate of the perfusate/analyte, which is required for an adequate buildup of glucose in the perfusate. This typically causes a time delay from the sampling to the evaluation of around 10 minutes. Moreover, a considerable expense is necessary in order to operate the measurement cell and the reference cell under the same external, especially thermal, conditions, so that any differences will not negatively affect the measurement result. Document DE 20 2007 019 544 U1 teaches the same measurement principle.

SUMMARY OF THE INVENTION

The problem which the present invention proposes to solve is therefore to provide a glucose sensor and a method for the permanent determination of the blood sugar value, enabling a precise and timely in vivo determination of the blood sugar value which is permanently reliable and largely unfalsified by external influences.

The problem is solved by a glucose sensor and a method for determining a glucose value in blood or in interstitial fluid, comprising the steps of bringing a measuring probe coupled to a coupling surface of a first optical waveguide, which comprises a mirror arranged opposite the coupling surface of the first optical waveguide and a detection chamber between the coupling surface of the first optical waveguide and the mirror, containing a detection fluid for glucose and enclosed by a membrane having a separation capacity of at most 20 kDa, into contact with the blood or the interstitial fluid, wherein the glucose depending on a concentration gradient diffuses out from the blood or the interstitial fluid into the detection fluid or from the detection fluid into the blood or the interstitial fluid, light is coupled into the first optical waveguide and guided through the latter to the detection chamber, reflected at the mirror and taken back through the first optical waveguide, while light in dependence on the glucose concentration in the detection fluid is absorbed in the detection chamber, and an intensity of the light returning from the detection chamber is measured.

The glucose sensor according to the invention comprises a catheter, having one or more openings in the region of its distal end, a first optical waveguide arranged in the catheter with a coupling surface at its distal end, a measuring probe arranged in the region of the distal end of the catheter and coupled to the coupling surface of the first optical waveguide, having a mirror disposed opposite the coupling surface of the first optical waveguide and a detection chamber between the coupling surface of the first optical waveguide and the mirror, a detection fluid for glucose in the detection chamber, and a membrane, which encloses at least the detection chamber filled with the detection fluid and which is not permeable to cells or most proteins, yet is permeable to glucose. For this purpose, the membrane has a separation capacity of at most 20 kDa. In this way, it is ensured that the detection chamber is protected against the incursion of blood cells and larger molecules such as fats, proteins, and others, while the detection fluid and glucose can diffuse through the membrane.

Preferably, the detection fluid used is an electrolyte-containing, isotonic, aqueous solution, in order to limit substantially to glucose the exchange through the membrane for purposes of concentration equalization. In particular, so-called Ringer solution will be considered as the detection fluid.

If the glucose concentration in the detection fluid is initially zero, for example, or at least less than that in the bodily fluid, the exchange will occur at first from the bodily fluid in the direction of the detection fluid. If the probe remains in the blood stream and the glucose concentration in the blood decreases over the course of time, a diffusion of the glucose through the membrane will occur in the reverse direction.

The optical waveguide with coupled measuring probe is also called hereinafter the measurement channel.

Accordingly, the method according to the invention specifies that a measuring probe coupled to the coupling surface of a first optical waveguide, which comprises a mirror arranged opposite the coupling surface of the first optical waveguide and a detection chamber between the coupling surface of the first optical waveguide and the mirror, containing a detection fluid for glucose and enclosed by a membrane which is not permeable to cells and proteins yet is permeable to glucose, is brought into contact with the blood or the interstitial fluid, wherein the glucose depending on the concentration gradient diffuses out from the blood or the interstitial fluid into the detection fluid or from the detection fluid into the blood or the interstitial fluid, light is coupled into the first optical waveguide and conducted through the latter to the detection chamber, reflected at the mirror, and taken back through the first optical waveguide, while light in dependence on the glucose concentration in the detection fluid is absorbed in the detection chamber, and the intensity of the light returning from the detection chamber is measured.

For this, the device preferably comprises furthermore a measuring and evaluating device, which comprises a detector coupled to the first optical waveguide and designed to measure the intensity of the light returning from the detection chamber through the first optical waveguide.

Unlike the method first mentioned in the introduction, the measurement principle of the invention is not based on a chemical reaction, but rather on an absorption of light. The patent application DE 10 2009 010 955 A1 likewise mentioned above, and also the article, thus constitute the category. Yet unlike what is mentioned in the patent application, an absorption measurement does not occur directly in the blood, but instead in a measurement fluid kept separate from the blood, yet interacting with the blood by way of a diffusion through a semi-permeable membrane. The latter is also known in principle from the aforementioned article, however the absorption measurement there does not occur directly in the contact area with the blood or the interstitial fluid, but instead at a distance from this, outside the human body, which leads to the above explained problems. The invention for the first time makes it possible to determine the change in the glucose concentration occurring in the blood or in the interstitial fluid indirectly through a detection fluid, yet directly in the body and thus free from the mentioned negative effects, such as an accumulation of blood cells, varying ambient conditions or a long measurement duration, and thus not least of all very precisely.

The measuring probe is arranged in the region of the distal end of the catheter, where it comes into contact directly in the tissue or the blood stream of the patient with the interstitial fluid or blood (hereinafter subsumed under the term "bodily fluid"), which penetrates into the one or more openings in the catheter. The opening in the most simple instance can be formed in that the catheter is fashioned as a cannula open at the end face and/or comprises an outer wall with a perforated section, which is configured in the axial direction preferably at the height of the measuring probe, and thus encloses it partly or entirely. The catheter in particular forms the supporting structure for the membrane in the area of the measuring probe.

A cannula open at the end face or even pointed is more of a disadvantage for long-term residence in the body. Preferably, therefore, the catheter is closed at the end face. It is preferably inserted into the body by means of a pointed sleeve or cannula, after which the sleeve is again removed and the catheter remains in the body.

If the bodily fluid makes contact with the membrane, depending on the glucose concentration in the bodily fluid a diffusion-controlled exchange of glucose through the membrane will occur, until the glucose concentration in the detection fluid and in the bodily fluid is substantially equal. (A complete equalization will only be reached asymptotically.) The light which is coupled into the first optical waveguide at its proximal end leaves it at its distal end via the coupling surface and enters the detection chamber. Here, it passes twice through the detection fluid on its path to the opposite positioned mirror and from the mirror back to the coupling surface.

The glucose is detected in the near infrared spectrum indirectly by the shifting of an absorption band of water as a result of an interaction with the glucose. This shift can be registered by absorption measurement at certain characteristic wavelengths. It has proven to be advantageous for this to use light with a wavelength between 800 nm and 3000 nm, especially in the overtone band region of around 1000 nm to 2500 nm. The attenuated light is then taken back through the same first optical waveguide and supplied at its proximal end to the detector of the measuring and evaluating device. Here, an intensity measurement is done in familiar manner, from which the absorption and thus the glucose concentration in the detection fluid or the bodily fluid can be ascertained.

For this purpose, preferably at the proximal end of the optical waveguide there is provided a beam divider or a semitransparent mirror, which lets through the incoming light to the optical waveguide and deflects the guided light back to the detector. Preferably, a 1×2 coupler is used.

Preferably, the measuring and evaluating device is coupled to a reference channel and designed to measure an intensity of the light in the reference channel and compare it to the intensity of the light returning from the detection chamber through the first optical waveguide. In terms of method, this modification of the invention specifies that a light beam is at first divided, then a first portion of the light is coupled into the first optical waveguide and a second portion of the light is supplied to a reference channel, in which the intensity of the second portion of the light is measured, and then compared to the measured intensity of the light returning from the detection chamber.

Thus, in the reference channel a reference measurement of the light emitted by a light source takes place, enabling a direct subtraction of light intensity fluctuations from the measurement signal. This method is called hereafter a difference measurement. The difference measurement is generally discussed, for example, in the document DE 10 2004 055 032 A1.

Especially preferably, there is provided a reference probe arranged in the catheter in the vicinity of the measuring probe and a second optical waveguide arranged in the catheter with a coupling surface at its distal end, wherein the reference probe and the second optical waveguide form the reference channel and the reference probe is coupled to the coupling surface of the second optical waveguide. The reference probe has a mirror arranged opposite the coupling surface of the second optical waveguide and a reference measuring chamber between the coupling surface of the second optical waveguide and the mirror with a reference medium of constant glucose concentration and the measuring and evaluating device comprises a detector coupled to the second optical waveguide.

In connection with this design, we shall speak in the following of an "absorption difference measurement". The layout of the reference measuring chamber and the layout of the detection chamber are very similar, and especially in their geometrical dimensions they are even identical. The same holds for the first and the second optical waveguide. In this way, and moreover also due to the physical proximity of the reference probe and the measuring probe, the beam path in the reference channel and in the measurement channel is for the most part identical. Moreover, the measurement conditions, especially the thermal conditions to which the measuring probe and the reference probe are exposed during the measurement, are practically identical. A comparing of the intensity measurements in the measurement channel and the reference channel therefore enables a subtraction of almost all systematical errors and thus a further distinct enhancement of the precision of the measurement. In this way, it is possible to achieve a measurement precision of not more than 5% mean absolute relative error (MARE). A further improvement can be achieved if, advantageously, the number of wavelengths used is increased, i.e., by using light of several discrete wavelengths instead of light with one wavelength during the measurement.

The absorption difference measurement can be carried out preferably with two separate detectors for the measurement channel and the reference channel. Although the same detector can also be used for the reference channel that is coupled to the measurement channel, this requires a sequential measurement, which runs counter to certain advantages of the absorption difference measurement and therefore will only be considered in connection with pulsed measurement at short time intervals.

The reference medium is preferably essentially water or an aqueous solution, because the changes in the water absorption upon dissolution of glucose are especially pronounced. In order for the reference probe to provide the most reliable possible comparison value, especially preferably one will use an aqueous solution of equivalent effect in regard to the measurement method, i.e., the absorption behavior, and again preferably without glucose, fats or proteins. Detection fluid and reference medium accordingly need not be solutions of perfectly identical ingredients, apart from the glucose concentration, but instead it is enough for them to have the same effect in regard to the measurement method/absorption behavior.

Naturally, these conditions are best fulfilled when the reference medium and the detection medium are identical except for the glucose concentration. Therefore, according to one advantageous embodiment of the invention, the same isotonic solutions are used as reference medium in the beginning in the reference measuring chamber, for example the mentioned Ringer solution. The glucose concentration then changes only in the detection chamber as a consequence of the measurement.

One advantageous embodiment of the glucose sensor specifies that the membrane encloses the detection chamber filled with the detection fluid between the coupling surface of the first optical waveguide and the mirror. "Encloses" in the sense here means that the detection chamber is defined as a volume bounded all around. The detection fluid is enclosed therein not in the narrower sense, because it stands in an exchange by diffusion through the membrane with the bodily fluid surrounding the catheter. Even so, it is a physically bounded volume with detection fluid, as opposed to the systems according to DE 20 2007 019 544 U1, for example. This embodiment requires no technical expense to move the detection fluid in a circulation or a permanent exchange.

In this embodiment, the reference probe preferably has a partition, where the partition encloses the reference measurement chamber filled with the reference medium between coupling surface of the second optical waveguide and the mirror and holds back the reference medium therein.

Once again, a very similar design layout of the measuring probe and the reference probe is emphasized here, while the partition is functionally distinguished from the membrane in that it is not (also) permeable to glucose and especially preferably not to the reference medium, so that the glucose concentration in the reference medium remains constant. The detection chamber and the reference measuring chamber are thus fluidically separated in this embodiment.

An alternative configuration to two separate detection and reference measurement chambers calls for the glucose sensor to have a flow channel, in which the reference probe and the measuring probe are arranged and which can receive the flow of the detection fluid or reference medium, while the membrane forms a wall section of the flow channel in the region of the measuring probe and holds the detection fluid back in the flow channel.

Furthermore, the glucose sensor in this configuration preferably comprises a delivery device, which is connected to the flow channel and designed to generate a flow of the detection fluid or the reference fluid through the flow channel.

Under these circumstances, the reference probe and the measuring probe are especially preferably arranged in this sequence one behind the other in the flow direction in the flow channel.

In the above described alternative configuration, the detection fluid as well as the reference medium are no longer enclosed in the detection chamber of the measuring probe or the reference measuring chamber of the reference probe. Instead, the detection chamber and the reference measuring chamber form open measuring chambers, receiving the continuous flow of the detection or reference fluid delivered through the flow channel. The flow channel is formed in the area of the reference probe preferably by an inner tube arranged in the catheter and in the area of the measuring probe by the membrane arranged in the catheter. When the flowing detection fluid first passes through the reference probe it has not yet flowed past the membrane and therefore has not yet made contact with the glucose from the bodily fluid. Therefore, the detection fluid at first has the functional purpose of the reference medium with (up to that point) constant glucose concentration. After it has passed through the reference probe and reached the section of the membrane, a diffusion-controlled glucose exchange takes place, so that the measuring probe arranged in the area of the membrane makes contact with altered glucose concentration in the detection fluid. Two design configurations of the flow channel shall be explained below with the help of the sample embodiments.

Especially preferably, the first and/or the second optical waveguide comprises a multimode or a monomode fiber. The multimode fiber is preferable, because it does not limit the optical power as much as the monomode fiber and thus the measurement sensitivity is on the whole better. Basically, the first and/or the second optical waveguide can be formed from a single fiber or from fiber bundles.

By a glucose sensor in the sense of this document is meant both a unit with or without its own light source and likewise with or without its own measuring and evaluating device, i.e., in particular, also the bare catheter with waveguide and measuring probe. However, preferably it comprises its own light source coupled to the first optical waveguide and, if present, to the reference channel.

The reference channel is preferably powered by the same light source which also powers the measurement channel, because then it is possible to eliminate for the most part fluctuations in light intensity at the source side.

In this case, the glucose sensor comprises a beam divider hooked up between the light source and the first optical waveguide, which is designed to couple a first portion of the light into the first optical waveguide and supply a second portion of the light to a reference channel.

Accordingly, the method according to the invention specifies that the light beam coming from the light source is at first divided, then a first portion of the light is coupled into the first optical waveguide and the second portion of the light is coupled into the second optical waveguide and guided through this to the reference measurement chamber, reflected on the mirror, and returned through the second optical waveguide, while light is absorbed in the reference measuring chamber depending on the glucose content in the reference medium, and the intensity of the light returned from the reference measuring chamber is measured and compared with the measured intensity of the light returned from the detection chamber.

The light source, especially the infrared light source, preferably comprises an LED or several LEDs.

BRIEF DESCRIPTION OF THE DRAWINGS

Further details and benefits of the invention will be further explained in the following with the aid of sample embodiments, making reference to the figures. There are shown.

DETAILED DESCRIPTION OF THE INVENTION

Figure 1:
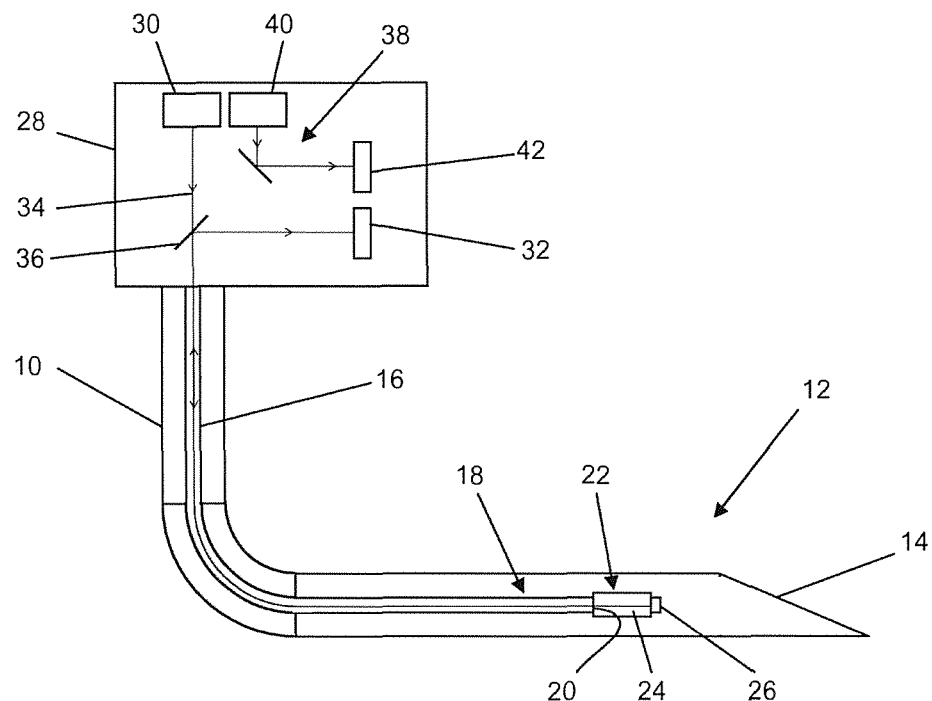
FIG. 1, a first sample embodiment of the glucose sensor with an optical waveguide in a catheter and separate reference channel outside of the catheter.

The sample embodiment of the glucose sensor of the invention per FIG. 1 comprises a catheter 10 with a distal end 12, which is shaped as a needle tip or cannula and has an opening 14 at its front end. In the catheter 10 is arranged an optical waveguide 16, having a coupling surface 20 at its distal end 18. Moreover, in the region of the distal end 12 of the catheter 10 there is arranged a measuring probe 22 which is optically coupled to the coupling surface 20 of the optical waveguide 16. The measuring probe 22 comprises a detection chamber 24 filled with a detection fluid for glucose and a mirror 26 arranged facing the coupling surface 20. Details shall be explained below with the aid of FIGS. 3 to 5.

The glucose sensor in this form can be injected subcutaneously or into a person's blood stream, whereupon blood or interstitial fluid penetrates by virtue of capillary forces through the end opening 14 into the cavity of the catheter 10 and comes into contact there with the measuring probe 22.

Furthermore, FIG. 1 shows, schematically simplified, a housing 28, in which both a light source 30 and a measuring and evaluating device are assembled. The measuring and evaluating device for its part comprises a detector 32 coupled to the optical waveguide 10 and furthermore an electronic reading unit, not shown. This is designed to measure the intensity of the light returning from the detection chamber 24 through the optical waveguide 10 and optionally to display it or put it out as a control signal, for example for a connected insulin pump.

The light, indicated by the beam 34, is returned within the optical waveguide 16 on the same path by which it arrives at the measuring probe 22. Therefore, the returning beam must be deflected at a beam divider 36 or a one-sided or partly transparent mirror and routed to the detector 32.

Moreover, an entirely separate reference channel 38 is shown in the housing 28, comprising its own light source 40 and its own detector 42. The reference channel in this simple embodiment serves merely to detect any fluctuations in the power supply voltage or in the ambient conditions, especially the temperature of the electronics, and to eliminate their effects on the measurement signal by comparing the reference signal to the measurement signal and preferably subtracting it. Of course, this only represents one of various options for the monitoring of systematic errors. A more precise monitoring of systematic errors occurs, for example, when the reference channel 38 and the measurement channel use a common light source, whose beam is divided before entering the optical waveguide and coordinated with a detector of the reference channel. A further improved reference measurement is shown by the sample embodiment of FIG. 2.

Figure 2:
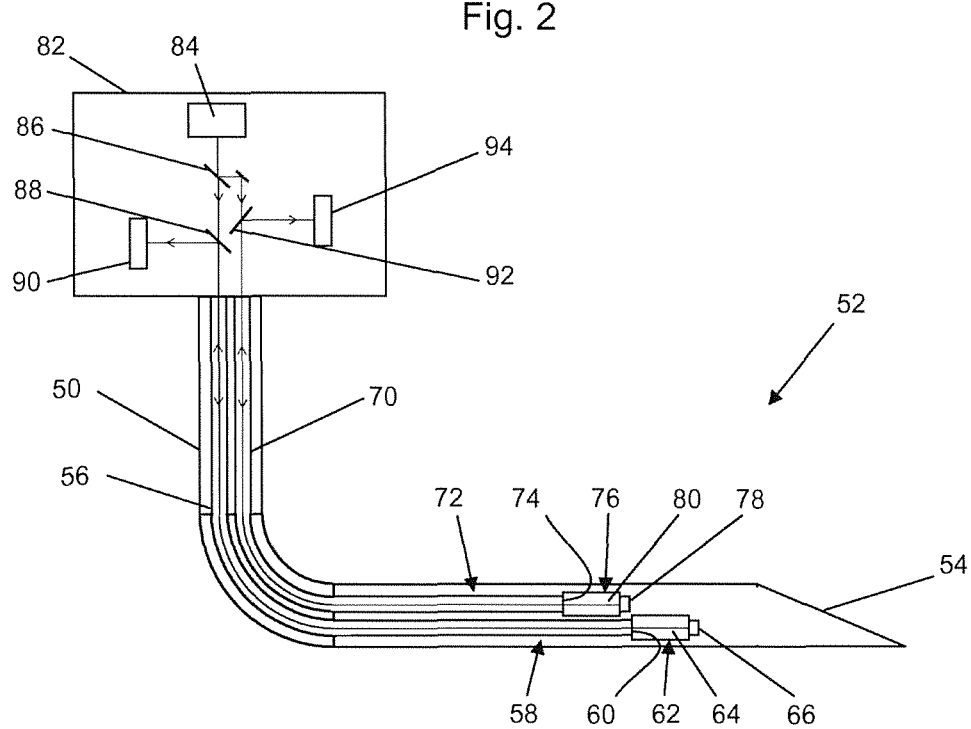
FIG. 2, a second sample embodiment of the glucose sensor with a first optical waveguide and measuring probe and a second optical waveguide and reference probe in a catheter.

The glucose sensor of FIG. 2 comprises a catheter 50 with a distal end 52 shaped as a needle tip or cannula, at the end of which once again there is an opening 54. In the catheter 50 there is arranged a first optical waveguide 56, at whose distal end 58 is provided a coupling surface 60 for the coupling of light into a measuring probe 62. The measuring probe 62 as in the previous example comprises a detection chamber 64 between the coupling surface 60 and a mirror 66 arranged opposite the coupling surface and it contains (at least during the measurement) a detection fluid for glucose in the bodily fluid.

The glucose sensor, in contrast to the example in FIG. 1, moreover comprises a second optical waveguide 70 in the catheter 50, having at its distal end 72 a coupling surface 74, to which a reference probe 76 is optically coupled. The reference probe 76 comprises a mirror 78 disposed opposite the coupling surface 74 of the second optical waveguide 70 and a reference measuring chamber 80 between the coupling surface 74 and the mirror 78, which is filled with a reference medium with constant glucose concentration. The second optical waveguide 70 and the reference probe 76 form here the reference channel.

The glucose sensor in this sample embodiment moreover comprises in a schematically depicted housing 82 a light source 84, which supplies light to both the measuring probe 62 and the reference probe 76. For this purpose, the light emitted by the light source 84 is divided by means of a beam divider 86 into two beams, one of which is coupled into the first optical waveguide 56 and one into the second optical waveguide 70. The light returning from the measuring probe 62 through the first optical waveguide 50 arrives by way of another beam portion 88 or a one-sided or partly transparent mirror at a first detector 90 of a measuring and evaluating device likewise present in the housing 82. Similarly, the light returning from the reference probe 76 via the second optical waveguide 70 is deflected by a third beam divider 92 and routed to a second detector 94 of the measuring and evaluating device.

In contrast with the sample embodiment of FIG. 1, the measurement conditions of the reference channel are made even more similar to the measurement conditions of the measurement channel. This is due primarily to the physical proximity between the measuring probe 62 and the reference probe 76, which are both located in the region of the distal end 52 of the catheter 50, and the largely identical guidance of the light to and from the measuring and evaluating device. Moreover, the identical conditions are also created in that both channels use the same light source 84. As a result, fluctuations in the light intensity caused at the source can be eliminated and differences in the physical conditions during the measurement (temperature differences) avoided, by comparing the measurement signal with the reference signal and subtracting the latter from the former.

Figure 3:
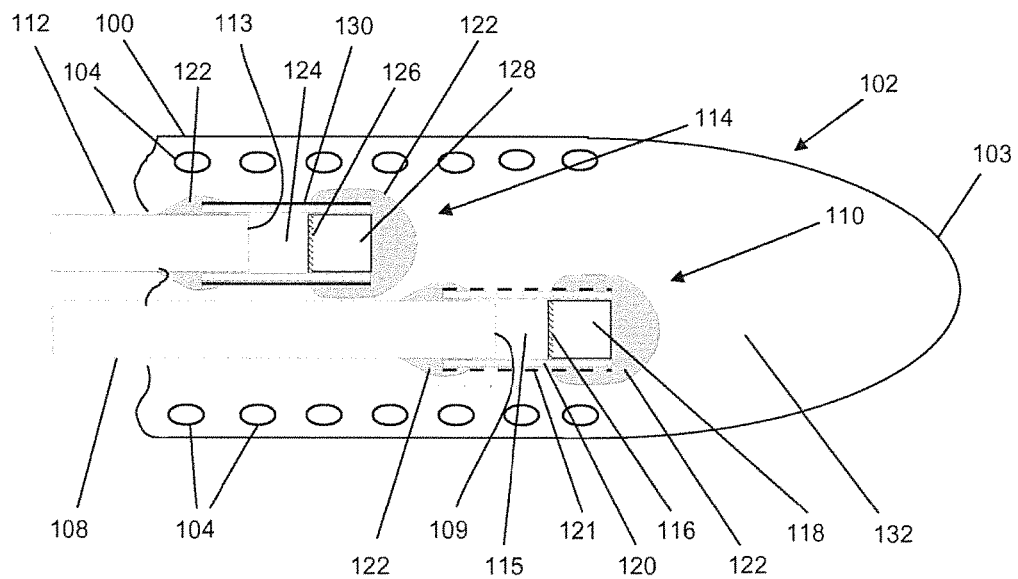
FIG. 3, a cutout view of the distal end of the catheter with a first embodiment of the measuring probe and the reference probe.

FIG. 3 is a more detailed representation of the catheter 100 in the region of its distal end 102. As an example, this embodiment comprises a rounded catheter tip 103. The catheter has several openings 104 in the form of a peripheral perforation of the catheter wall, through which the bodily fluid can get into a cavity 132 of the catheter. The catheter is inserted in the body at the desired position, preferably with the aid of a hollow needle, and then the hollow needle is drawn out.

As explained in connection with the sample embodiment of FIG. 2, there are arranged in the catheter a first optical waveguide 108 with a measuring probe 110 optically coupled to its end-side coupling surface 109 and a second optical waveguide 112 with a reference probe 114 optically coupled to its end-side coupling surface 113. The measuring probe 110 comprises, in turn, a detection chamber 115 filled with a detection fluid for glucose and a mirror 116 disposed opposite the coupling surface 109. The mirror 116 here is formed, for example, as a mirrored surface of a piece of fiber 118.

The detection chamber 115 in this embodiment is bounded around its periphery by a membrane 120 which is permeable to glucose, but not to cells and most proteins. The membrane for its part is enclosed around its periphery by a supporting element 121, which confers the necessary mechanical stability on the membrane and holds the mirror 116 and the coupling surface 109 at a defined distance. The supporting element 121 can be formed from a rigid metal or plastic tube, which is perforated on at least one section for purposes of the glucose exchange. The supporting element 121 is connected together with the membrane 120 at one axial end to the optical waveguide 108 and at the other axial end to the fiber piece 118, while the joints 122 at both ends also form a seal for the detection chamber 115. The supporting element 121 and the membrane 120 can be glued fluid-tight for this purpose to the optical waveguide 108 and the fiber piece 118, for example by means of silicone adhesive.

The structural design of the reference probe 114 is identical. This as well comprises a cavity, the reference measuring chamber 124, as well as a mirror 126 arranged opposite the coupling surface 113 of the second optical waveguide 112, which is likewise formed by a one-sided mirrored piece of glass fiber 128. The reference measuring chamber 124 formed between the coupling surface 113 and the mirror 126 is enclosed by a partition 130, which encapsulates the reference medium situated therein and separates it entirely from the surrounding bodily fluid in the cavity 132 in the catheter tip 102, so that no exchange of glucose, detection fluid or other substances can occur between the reference measuring chamber 124 and the cavity 132. The partition here is likewise designed with a membrane located on the inside and a stiffening supporting element surrounding the membrane at its periphery. But the supporting element here is fashioned as a circumferentially enclosed tube for purposes of sealing. Basically, no membrane is needed for the reference probe, since no permeability is required. But in order to create identical conditions in the reference probe 114 and the measuring probe 110, especially the same thermal conditions, a largely identical design is preferable. In this case as well, the optical waveguide 112 as well as the piece of fiber 128 forming the mirror 126 is glued fluid-tight into the tubular or hoselike partition section 130 in the area of the joints 122.

If the needle-shaped distal end 102 of the catheter 100 is injected, bodily fluid gets in through the openings 104 and 106 to the cavity 132 of the catheter and makes contact with the membrane 120 of the measuring probe 110 as well as the partition 130 of the reference probe 114. In this way, the measuring probe and the reference probe find themselves at the same thermal level. However, the glucose can only get into the detection chamber 115 through the membrane 120, where a loss of intensity occurs by virtue of an absorption of the light coupled in, which can be detected with the previously represented measuring and evaluating device of FIG. 2 and compared to the measurement result of the reference channel.

Figure 4:
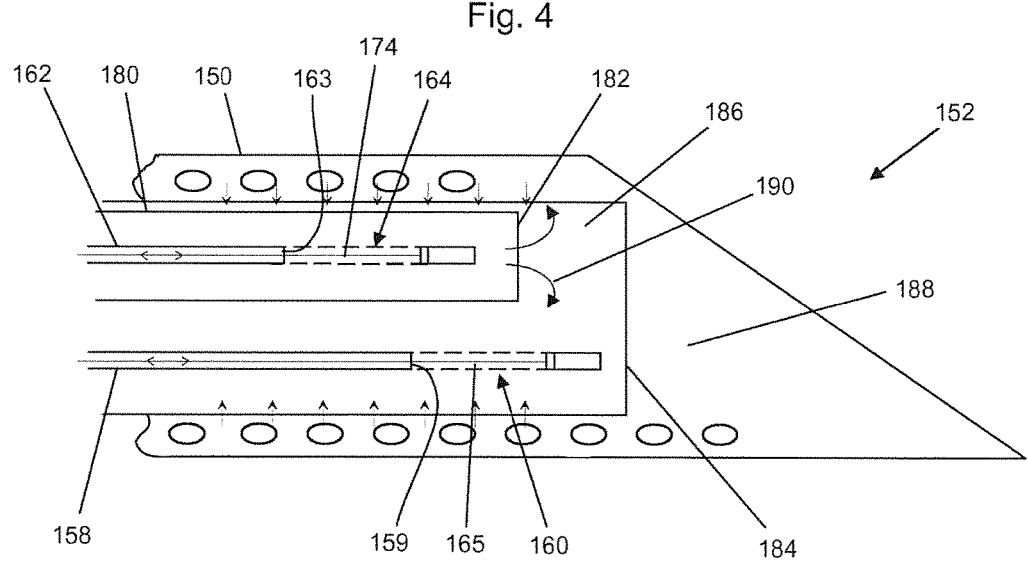
FIG. 4, the distal end of the catheter with a second embodiment of the measuring probe and the reference probe and FIG. 5, the distal end of the catheter with a different arrangement of the measuring probe and the reference probe.

FIG. 4 shows a second configuration of the catheter 150 in the region of its distal end 152, whose needle-shaped tip has the same shape as the previously described sample embodiment, along with openings. The glucose sensor also comprises a first optical waveguide 158 with a coupling surface 159 at its distal end, to which the measuring probe 160 is coupled in the above described manner. Once again, the second optical waveguide 162 has a coupling surface 163 with reference probe 164 coupled to it.

In contrast with the previously described sample embodiment, however, the detection chamber 165 and the reference measuring chamber 174 are not individually sealed off, but instead fashioned with an open wall, so that an exchange of the reference medium or the detection fluid, hereinafter subsumed under the term perfusate, can occur. This takes placed in controlled manner, in that an inner tube 180 is provided, surrounding the second optical waveguide 162 and the reference probe 164, and being open at its distal end 182. Furthermore, the inner tube 180 together with the first optical waveguide 158 and the measuring probe 160 is surrounded by a semipermeable membrane 184, which divides the interior of the catheter 150 in an internal chamber 186, which is tight to the perfusate but open to the glucose, and an external chamber 188. The inner tube 180 is attached, at the pressure side, at its proximal end (not shown) to a delivery device (not shown). The internal chamber 186 inside the membrane 184 is connected to the suction side of the delivery device. The delivery device is designed to delivery the perfusate and generates a flow of the perfusate through the inner tube 180 into the internal chamber 186, as indicated by the flow arrows 190. Thus, the inner tube 180 forms, together with the membrane 184, a flow channel in which the reference probe 164 and, downstream, the measuring probe 160 are arranged. This ensures that the reference probe 168 is bathed in a reference medium with constant glucose concentration, and the medium then gets into the internal chamber 186, where it takes up or surrenders glucose through the membrane 184 by virtue of diffusion. It then makes contact with the measuring probe 160, where a different absorption of the light can be detected as a function of the glucose.

Figure 5:
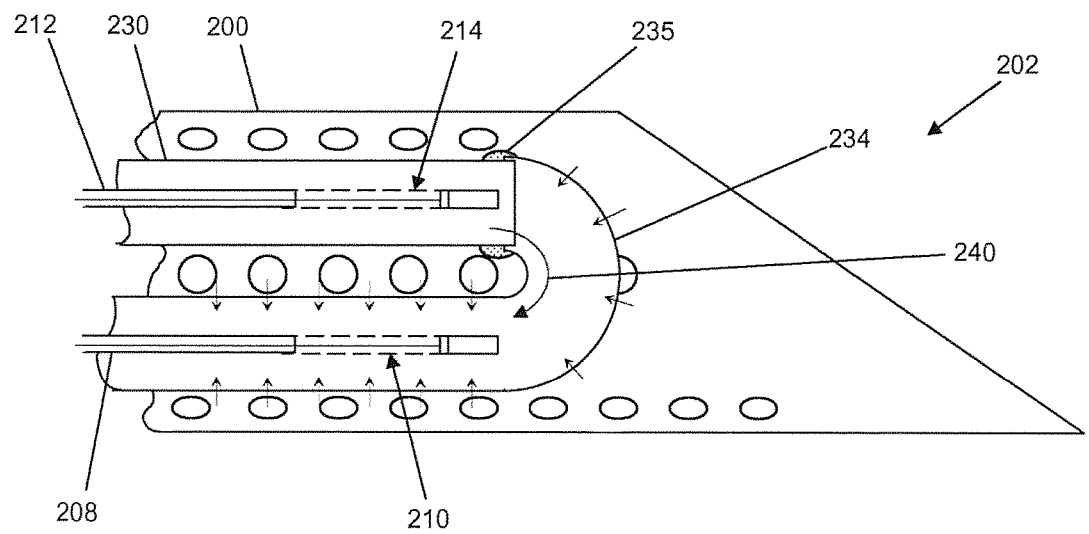

The configuration of FIG. 5 resembles that of FIG. 4 in functional respect, since a flow channel is also configured here. However, the design measures are different. First of all, there are also provided here in a catheter 200 in the region of its distal end 202 a first optical waveguide 208 with a measuring probe 210 coupled to it and a second optical waveguide 212 with a reference probe 214 coupled to it. Likewise in this sample embodiment the measuring probe 210 and the reference probe 214 are fashioned with an open wall. Once more, the second optical waveguide 214 and the reference probe 214 are surrounded by an inner tube 230. The major design difference consists in that the semipermeable membrane 234 is glued, fluid-tight, to the inner tube 230, as indicated by the joints 235, and continues the flow channel of the inner tube 230 with substantially the same cross section. The semipermeable membrane 234 is fashioned as a tube or hose. This time, it only surrounds the measurement cell 210 and not also the inner tube.

Like before, the inner tube 230 can be connected at the pressure side and the membrane 234 at the suction side to a delivery device. Thus, the perfusate can be delivered with a flow 240 from the reference probe 214 to the measuring probe 210. Thus, here as well it is assured that first the reference probe 214 makes contact with a reference medium with constant glucose concentration and only after taking up glucose is contact made with the measuring probe 210.

Downstream from the measuring probe 210, the membrane 234 can pass, in a manner not shown, into a second inner tube, which is completely fluid-tight, because no longer is any permeability to glucose required there. The first and, if present, the second inner tube in all embodiments, as well as the catheters, are preferably made of refined steel, transitional metal such as titanium, precious metals or plastics.

LIST OF REFERENCE SYMBOLS

10 Catheter
12 Distal end of catheter
14 Opening of catheter
16 First optical waveguide
18 Distal end of first optical waveguide
20 Coupling surface of first optical waveguide
22 Measuring probe
24 Detection chamber
26 Mirror
28 Housing
30 Light source
32 Detector
34 Light beam
36 Beam divider
38 Reference channel
40 Light source
42 Reference detector
50 Catheter
52 Distal end of catheter
54 Opening of catheter
56 First optical waveguide
58 Distal end of first optical waveguide
60 Coupling surface of first optical waveguide
62 Measuring probe
64 Detection chamber
66 Mirror
70 Second optical waveguide
72 Distal end of second optical waveguide
74 Coupling surface of second optical waveguide
76 Reference probe
78 Mirror
80 Reference measuring chamber
82 Housing
84 Light source
86 Beam divider
88 Beam divider
90 Detector
92 Beam divider
94 Detector
100 Catheter
102 Distal end
103 Rounded catheter tip
104 Opening
108 First optical waveguide
109 Coupling surface of first optical waveguide
110 Measuring probe
112 Second optical waveguide
113 Coupling surface of second optical waveguide
114 Reference probe
115 Detection chamber
116 Mirror
118 Fiber piece
120 Membrane
121 Supporting element
122 Joint
124 Reference measuring chamber
126 Mirror
128 Fiber piece
130 Partition
132 Internal chamber of catheter
150 Catheter
152 Distal end of catheter
158 First optical waveguide
159 Coupling surface of first optical waveguide
160 Measuring probe
165 Detection chamber
162 Second optical waveguide
163 Coupling surface of second optical waveguide
164 Reference probe 174 Reference measuring chamber
180 Inner tube
182 Distal end of inner tube
184 Membrane
186 Internal chamber
188 External chamber
190 Flow direction
200 Catheter
202 Distal end of catheter
208 First optical waveguide
210 Measuring probe
212 Second optical waveguide
214 Reference probe
230 Inner tube
234 Membrane
235 Joint
240 Flow direction

What is claimed is:

1. A glucose sensor, comprising:
a catheter, having one or more openings in a region of its distal end,
a first optical waveguide arranged in the catheter with a coupling surface at its distal end,
a measuring probe disposed in the region of the distal end of the catheter and coupled to the coupling surface of the first optical waveguide, having a mirror disposed opposite the coupling surface of the first optical waveguide and a detection chamber between the coupling surface of the first optical waveguide and the mirror,
a detection fluid for glucose in the detection chamber,
a membrane, which encloses at least the detection chamber filled with the detection fluid and having a separation capacity of at most 20 kDa, and
a light source coupled to the first optical waveguide, wherein the light source is an infrared light source providing light with a wavelength between 800 nm and 3000 nm.

2. A glucose sensor according to claim 1, further comprising a measuring and evaluating device, which comprises a detector coupled to the first optical waveguide and designed to measure an intensity of light returning from the detection chamber through the first optical waveguide.

3. The glucose sensor according to claim 2, wherein the measuring and evaluating device is coupled to a reference channel and designed to measure an intensity of the light in the reference channel and compare it to the intensity of the light returning from the detection chamber through the first optical waveguide.

4. The glucose sensor according to claim 3, further including a reference probe, which is arranged in the catheter in the vicinity of the measuring probe and a second optical waveguide arranged in the catheter with a coupling surface at its distal end, wherein the reference probe and the second optical waveguide form the reference channel and the reference probe is coupled to the coupling surface of the second optical waveguide and comprises a mirror arranged opposite the coupling surface of the second optical waveguide and a reference measuring chamber between the coupling surface of the second optical waveguide and the mirror with a reference medium having a constant glucose concentration, and wherein the measuring and evaluating device comprises a detector coupled to the second optical waveguide.

5. The glucose sensor according to claim 4, wherein a reference medium is water or an aqueous solution.

6. The glucose sensor according to claim 4, wherein the reference probe comprises a partition, wherein the partition encloses the reference measuring chamber filled with the reference medium between the coupling surface of the second optical waveguide and the mirror and holds back the reference medium therein.

7. The glucose sensor according to claim 4, further including a flow channel, in which the reference probe and the measuring probe are arranged and which can receive the flow of detection fluid or the reference medium, wherein the membrane forms a wall section of the flow channel in the area of the measuring probe and holds back the detection fluid in the flow channel.

8. The glucose sensor according to claim 7, further including a delivery device, which is connected to the flow channel and designed to generate a flow of the detection fluid or the reference fluid through the flow channel.

9. The glucose sensor according to claim 8, wherein first the reference probe and then the measuring probe are arranged in the flow channel one after the other in the flow direction.

10. The glucose sensor according to claim 4, wherein the first and the second optical waveguide is a multimode fiber.

11. The glucose sensor according to claim 4, wherein the light source is coupled to the reference channel.

12. The glucose sensor according to claim 11, further including a beam divider hooked up between the light source and the first optical waveguide, which is designed to couple a first portion of the light into the first optical waveguide and supply a second portion of the light to the reference channel.

13. The glucose sensor according to claim 1, wherein the membrane is located between the coupling surface of the first optical waveguide and the mirror.

14. The glucose sensor according to claim 1, wherein the first optical waveguide is a multimode fiber.

15. The glucose sensor according to claim 1, wherein the light source comprises an LED or several LEDs.

16. A method for determining a glucose value in blood or in interstitial fluid, comprising the steps of bringing a measuring probe coupled to a coupling surface of a first optical waveguide, which comprises a mirror arranged opposite the coupling surface of the first optical waveguide and a detection chamber between the coupling surface of the first optical waveguide and the mirror, containing a detection fluid for glucose and enclosed by a membrane having a separation capacity of at most 20 kDa, into contact with the blood or the interstitial fluid, wherein the glucose depending on a concentration gradient diffuses out from the blood or the interstitial fluid into the detection fluid or from the detection fluid into the blood or the interstitial fluid, coupling light at a wavelength between 800 nm and 3000 nm into the first optical waveguide and guiding the light through the latter to the detection chamber, reflecting the light at the mirror and guiding back the light at the mirror through the first optical waveguide, while absorbing light in dependence on the glucose concentration in the detection fluid in the detection chamber, and measuring an intensity of the light returning from the detection chamber.

17. The method according to claim 16, comprising dividing a light beam, then coupling a first portion of the light into the first optical waveguide and supplying a second portion of the light to a reference channel, in which the intensity of the second portion of the light is measured, which is then compared with the measured intensity of the light returning from the detection chamber.

18. The method according to claim 17, wherein the reference channel has a second optical waveguide with a coupling surface and a reference probe in the vicinity of the measuring probe, which is coupled to the coupling surface of the second optical waveguide and comprises a mirror arranged opposite the coupling surface of the second optical waveguide and a reference measuring chamber between the coupling surface of the second optical waveguide and the mirror with a reference medium of constant glucose concentration, the second portion of the light is coupled into the second optical waveguide and guided through the latter to the reference measuring chamber, reflected at the mirror and taken back through the second optical waveguide, while light in dependence on the glucose concentration in the reference medium is absorbed in the reference measuring chamber, and the intensity of the light returning from the reference measuring chamber is measured and compared with the measured intensity of the light returning from the detection chamber.

* * * * *